United States Patent [19]

Bessho et al.

[11] Patent Number: 4,729,659
[45] Date of Patent: Mar. 8, 1988

[54] METHOD AND APPARATUS FOR MEASURING A LIQUID MOBILITY

[75] Inventors: Nobuo Bessho; Shozo Nishida, both of Tokyo, Japan

[73] Assignee: Japan Synthetic Rubber Co., Ltd., Tokyo, Japan

[21] Appl. No.: 909,920

[22] Filed: Sep. 22, 1986

[30] Foreign Application Priority Data

Sep. 30, 1985 [JP] Japan ................... 60-214738

[51] Int. Cl.$^4$ ............ G01N 21/90; G01N 15/04
[52] U.S. Cl. ..................... 356/342; 73/61 R; 73/866
[58] Field of Search ............ 73/61 R; 356/337, 338, 356/339, 246, 239, 342

[56] References Cited

U.S. PATENT DOCUMENTS

| 4,088,407 | 5/1978 | Schoeffel et al. | 356/246 X |
| 4,115,011 | 9/1978 | Brunsting | 356/246 |
| 4,348,107 | 9/1982 | Leif | 356/246 X |
| 4,435,080 | 3/1984 | Maly et al. | 356/337 X |
| 4,565,448 | 1/1986 | Abbott et al. | 356/246 X |
| 4,664,513 | 5/1987 | Webb et al. | 356/342 |

OTHER PUBLICATIONS

"Apparatus for Measuring Wetting Delays and Sorption Rates for Paper/Liquid Systems", B. L. Anderson et al., Coating Conference 1985, TAPPI Proceedings, pp. 47–54.
"Influence of Surfactant on the Gluing of Coated Board", P. Lepoutre et al., TAPPI Journal, vol. 68, No. 3, Mar. 1955; pp. 114–115.
"The 'Water Retention Test' in Evaluating Coding Color", Stinchfield, J. C., et al., TAPPI Journal, vol. 41, No. 2, Feb. 1985, pp. 77–79.
"Film Splitting as a New Technique for Measuring Water Retention of Coding Colors", Soemers, N. H., TAPPI Journal, vol. 53, No. 4, Apr. 1970, pp. 640–643.
"Possibilities and Limitations of High Solids Coding Colors", Reinhold, I., et al., TAPPI Coding Conference Proceedings, 1979, pp. 31–39.
"Coding Color Structure and Water Retention" Beck, U., et al., TAPPI Coding Conference Proceedings, 1983, pp. 47–54.

Primary Examiner—Daniel M. Yasich
Attorney, Agent, or Firm—Saidman, Sterne, Kessler & Goldstein

[57] ABSTRACT

Liquid mobility is judged by the steps of filling the specimen in a specimen chamber formed in a specimen bed made of a transparent material just up to the level of the upper surface of the specimen bed, of pressing a liquid-absorbent material keeper for keeping a liquid-absorbent material horizontally to make the liquid-absorbent material contact with the specimen bed from the upper side of the specimen chamber, and of continuously detecting an intensity of a scattered light coming from the specimen in the specimen chamber with an optical detector consisting of a light emitting source and a light receiver and being disposed on the side of the lower surface of the specimen bed while the liquid-absorbent material is forced to contact the specimen bed. The liquid mobility is grasped in a short period of time.

17 Claims, 7 Drawing Figures

METHOD AND APPARATUS FOR MEASURING A LIQUID MOBILITY

BACKGROUND OF THE INVENTION

1. Field of the Invention

The present invention relates to a method of measuring liquid mobility and an apparatus therefor, and specifically to a method of measuring separability of liquid in a slurry dispersion system comprising the liquid as a dispersion medium and an apparatus therefor

2. Description of the Prior Art

The recent strong inclination toward a higher coating speed and a higher concentration of a coating slurry has made coating conditions severer in coating techniques involved in the paper manufacturing industry, etc. Under such operation circumstances, for example, what physical properties and to what extent a latex must have for sufficiently securing an aptitude thereof to coating slurry with a coater head should be grasped in designing and developing the latex. Significant factors for the aptitude of the latex to coating include water retentivity and high speed fluidity.

The term "water retentivity" herein mentioned is a qualitative expression of a degree of retention of liquid as the dispersion medium in a dispersion, an example of which is a coating to be applied to a paper surface in the above-mentioned case, in a sense of whether or not the dispersion, for example, water is liable to separate in the dispersion.

Methods of measuring a liquid mobility like the above-mentioned water retentivity and apparatuses therefor which have heretofore been used include the following ones.

(1) S. D. Warren Method:

A water-absorbent material (base paper to be coated) is quietly placed or is placed with a slight pressure on a coating which is a mixture of a pigment, a latex, and water. When an electric conductivity of the water-absorbent material is measured on the side of the surface confronting air, the electric conductivity abruptly changes as soon as water absorbed in and spread through the water-absorbent material reaches the surface confronting air. The time required for the water to pass through the water-absorbent material is measured. Whether or not the water retentivity is good is judged based on the length of the above-mentioned time.

(2) Film Splitting Method:

A coating is spread in such a manner as to have a predetermined coating thickness. A water-absorbent material is placed on the coating for a predetermined short period of time, and then the water-absorbent article is removed. When water in a surface portion of the coating slurry is absorbed into the water-absorbent material, the dried state is observed in the surface portion of the coating. When water still remains, the wet state is observed. In view of this, the time required just for drying up of the surface portion is measured to judge the water retentivity of the coating liquid. The longer the time, the better the water retentivity.

(3) Pressurization Method:

According to this method, a coating liquid is filtrated with a filter. Whether or not the water retentivity is good is judged by an amount of the liquid filtrated for a predetermined period of time, while keeping the pressure constant.

(4) Standing Method:

A base paper as a water-absorbent material is coated with a coating slurry and allowed to stand. Water absorption by the base paper causes the surface of the coating slurry begin to dull or lose its glass. The time required till initiation of loss of glass is considered for judgement of whether or not the water retentivity is good.

These methods of measuring a liquid mobility and the apparatuses therefor involve a long time for measurement, which generally takes 10 sec. or longer. On the other hand, the period of time involved in the problem of water retentivity in the actual process is merely about 20 msec. Such a time difference makes those methods hardly match a real processing situation. Although a measurement of water absorption in an environment close to that involving real coating processing conditions, namely a measurement under a pressure, is necessary, there are no methods enabling this. In this connection, an operation of pressurization in the pressurization method (3) is merely for filtration. Further, the above-mentioned conventional methods involve a defect of liability to an individual difference of a measured value from measurer to measurer.

SUMMARY OF THE INVENTION

With a focus on the above-mentioned problems and with a view to solving the same, an object of the present invention is to propose a method of measuring a liquid mobility, which can allow a water absorption to be automatically judged under pressurized conditions just as in a coating processing in an extremely short time of about 100 msec.

Another object of the present invention is to provide an apparatus for embodying the method.

In the first aspect of the present invention, a method of measuring a liquid mobility comprises the steps of:

disposing a specimen at least partially containing liquid in a specimen chamber having a recessed form and made at least partially of a transparent material;

pressing a liquid-absorbent material capable of absorbing the liquid against an opening of the specimen chamber to absorb the liquid;

projecting a light onto the specimen from a light source so that the projected light is scattered from the specimen;

detecting an intensity of the scattered light coming from the specimen and measuring mobility characteristics of the liquid in accordance with a change in the intensity of the scattered light thus detected.

Here, the specimen may be a member selected from the group consisting of liquid, suspension, solution, and mixture thereof. The liquid-absorbent material capable of absorbing the liquid may be a member selected from the group consisting of paper, pulp fiber, non-woven fabric, woven fabric, and foam, and can cover at least the opening of the specimen chamber.

The optical detection means can comprise a light source directing the light at an angle not exceeding a critical angle over which total reflection occurs and a photo detecting device receiving the scattered light when a light is projected from the light source to obtain an electrical signal corresponding to the scattered light The specimen may be a member selected from the group consisting of liquid, suspension, solution, and mixture thereof, and the liquid-absorbent material capable of absorbing the liquid may be a member selected from the group consisting of paper, pulp fiber, non-woven fabric, woven fabric, and foam, and can cover at least the opening of the specimen chamber.

In the second aspect of the present invention, an apparatus for measuring a liquid mobility comprises:

a specimen chamber having an opening in one surface thereof for inserting a specimen at least partially containing a liquid, the specimen chamber being made at least partially of a trasparent material;

means for retaining a liquid-absorbent material capable of absorbing the liquid contained in the specimen and for pressing to make the liquid-absorbent material against the opening of the specimen chamber;

an optical detection means arranged on the side of the specimen chamber opposite the one surface, the detection means including a light source for projecting a light onto the specimen and a detector for detecting an intensity of a scattered light coming from the specimen;

a trigger means for detecting when the liquid-absorbent material contacts the specimen chamber to produce a trigger signal; and means for storing data indicative of the intensity of the scattered light detected by the optical detection means in response to the trigger signal.

Here, the specimen chamber may be a flat recess which has a diameter of 1 to 2 cm and a depth of 1 mm or less and is formed in a transparent specimen bed having a smooth surface and a thickness of 1 to 30 mm and made of glass, silica, transparent resin, or the like. The specimen may be a member selected from the group consisting of liquid, suspension, solution, and mixture thereof.

The liquid-absorbent material capable of absorbing the liquid may be a member selected from the group consisting of paper, pulp fiber, non-woven fabric, woven fabric, and foam, and can cover at least the opening of the specimen chamber. The optical detection means can comprise a light source directing the light at an angle not exceeding a critical angle over which total reflection occurs and a photo detecting device receiving the scattered light when a light is projected from the light source to obtain an electrical signal corresponding to the scattered light.

When a liquid mobility is measured in accordance with the present invention by the apparatus of the present invention, a switch of the apparatus is turned on after filling a specimen chamber of a specimen bed with a coating. A wiper is automatically or manually traversed just over the opening of the specimen chamber of the specimen bed to secure a predetermined uniform amount of the coating in the specimen chamber. A water-absorbent material is descended together with a head from the upper side to be pressed on the surface of the coating under a predetermined pressure. Just upon the pressing, an optical means for detecting a scattered light detects a scattered light coming from the coating, while the measured value is recorded in a transient memory. A measurer can judge the liquid mobility e.g., the water absorbency, from the recorded data.

The above and other objects, effects, features and advantages of the present invention will become more apparent from the following description of preferred embodiments thereof taken in conjunction with the accompanying drawings.

DETAILED DESCRIPTION OF PREFERRED EMBODIMENTS

Figure 1:
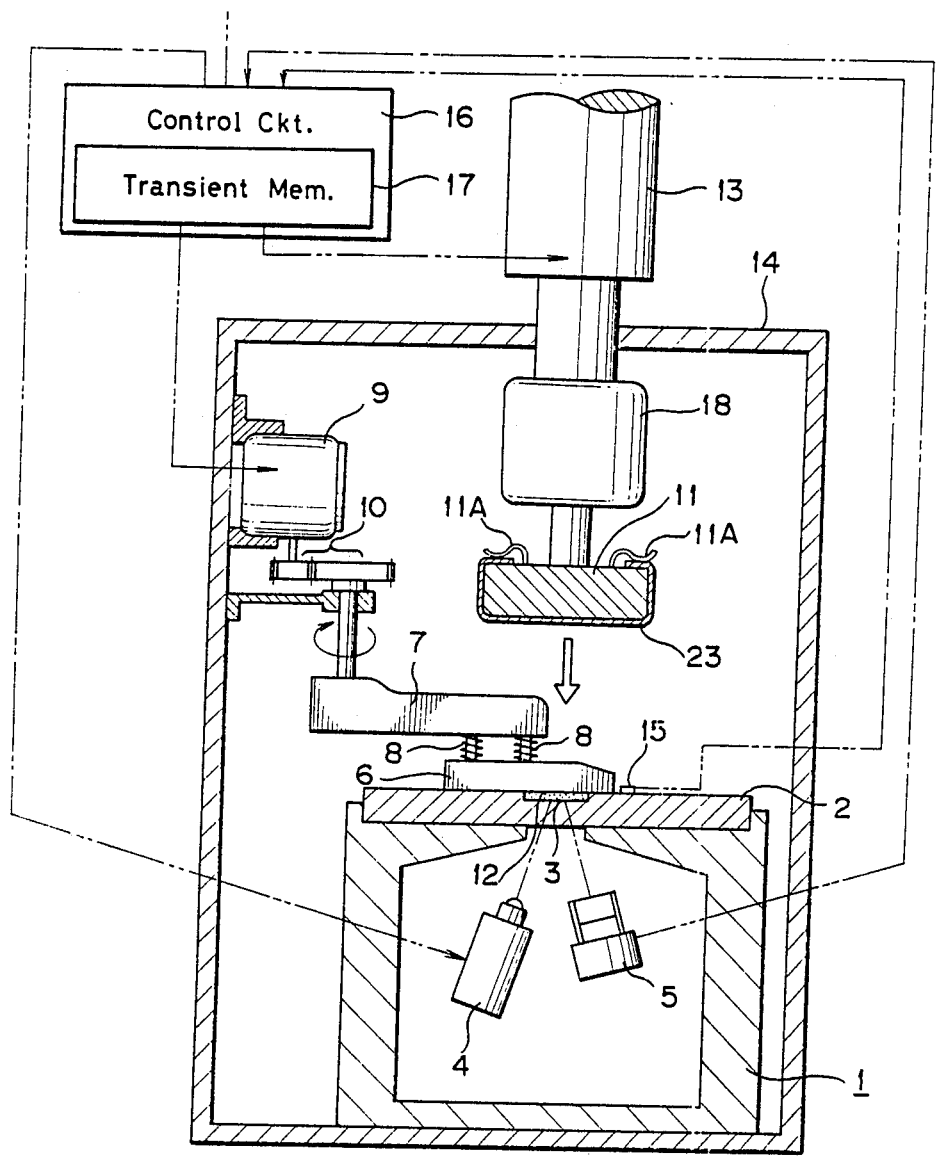
FIG. 1 is a schematic diagram showing an embodiment of an arrangement of an apparatus for measurement of a liquid mobility according to the present invention.

FIG. 1 shows an embodiment of the present invention. A measurement cylinder 1 constituting a dark box has a specimen bed 2 provided on the upper surface of the cylinder 1. Any material may be used in the specimen bed 2 in so far as it is not attacked by a specimen, and is transparent and hard to some extent. As preferred examples of such a material of the specimen bed 2, there can be mentioned transparent inorganic materials such as glass and quartz; and transparent organic materials such as methacrylic resins, polycarbonate resins, and polystyrene resins. Particularly preferred are hard glass and quartz. The thickness of the specimen bed is 0.1 to 30 mm, preferably 5 to 20 mm, to allow it to transmit a light with a wavelength adapted to a photosensitivity of a photodiode. The specimen bed 2 includes a specimen chamber 3 in the form of recess formed on the upper surface portion of the chamber 3. The shape, dimensions, depth and so on of the specimen chamber 3 can vary depending on the purpose. In this example, the specimen chamber 3 has a circular shape with a diameter of 1 to 2 cm and a depth of 1 mm or less, preferably 10 to 200 μm, most preferably 20 to 100 μm. It is desirable that the bottom portion of the specimen chamber 3 is flat in respect of measurement.

A light source 4 and a light receiver 5 are provided in the measurement cylinder 1. A laser light emitting unit is preferred as the light source 4. The light source 4, however, may be a usual incandescent lamp or the like. A photodiode or a photo multiplier is preferred as the light receiver 5. A part of a light projected from the light source 4 at a projection angle not exceeding the critical angle with respect to total reflection turns to a scattered light in the specimen chamber 3. The scattered light is reflected to be guided into the light receiver 5 so that an intensity of the scattered light is measured by the light receiver 5. Further, the whole specimen bed 2 is not necessarily required to be transparent. Specifically, if at least a portion of the specimen bed 2 corresponding to a light passage for the light detection means formed by the light source 4 and the light receiver 5 is transparent, the rest may be constituted by a material or a form capable of shielding light. In this case, background noises are removed from the detection output.

A wiper 6 is attached to a rotary arm 7, and can be biased toward the upper surface of the specimen bed 2 by a spring 8. A motor 9 is coupled to the arm 7 via a gear unit to rotate the arm 7 and hence the wiper 6 by way of the gear unit 10. In a measurement, the motor 9 can rotate the wiper 6 in a way as indicated by an arrow to shunt the wiper to such a position as not to obstruct the movement of the head 11. The wiper 6 may be, for example, a fluororesin plate having a good water repellency and a wedge form cross-section.

A head 11 is attached to a holder 18, and is so constructed as to be movable upward and downward together with the holder 18 via a piston 13. A case 14 contains the foregoing members. It is desirable that the case 14 is also kept in a state of a dark box to prevent background noises from being received by the light receiver 5 via the specimen chamber 3.

A liquid-absorbent material 23 for absorbing a liquid in a specimen 12 upon contact thereof with the specimen 12 contained in the specimen chamber 3 is fixed to a head 11. The head 11 is so formed from a water-nonabsorbent material such as a metal, a resin, or a hard rubber to have a flat lower surface. Retainers 11A serve to retain, for example, the edge portions of the liquid-absorbent material 23. The liquid-absorbent material 23 may be an adequate one chosen according to the purpose thereof, examples of which include highly water-absorbent papers without surface treatment, pulp fibers, non-woven fabrics, woven fabrics, and foams. The liquid-absorbent material 23 has a sufficient area a few times or more as large as that of the specimen chamber 3 so that it can fully cover the whole specimen chamber 3 from the upper side.

A contact sensor 15 is provided, for example, on the specimen bed 2 to detect a state of contact of the liquid-absorbent material 23 with the specimen 12 in the specimen chamber 3 when the head 11 falls down. A control circuit 16 is provided with a transient memory 17, a driving circuit for driving the motor 9 and the piston 13, and a central processing unit (CPU). Sequence control concerning a series of operations for measurement which will be described later can be performed by the control circuit 16.

The principle that an intensity of a scattered light coming from the specimen is varied in accordance with an amount of a liquid contained in a specimen subjected to the method of the present invention will now be described with reference to FIGS. 2 and 3.

In a dispersion containing a liquid as the dispersion medium, the surface thereof initially glitters but gradually dulls according to the lapse of time. In the case of a coating, it soon begins to assume a white color, and finally changes into a solid having a high degree of whiteness. As shown as (A) in FIG. 2, the initial stage involves the presence of solid fine particles 30, such as those in a polymer latex, suspended in the dispersion medium, for example, water 20, and in the initial stage an intensity of the scattered light is maintained at a given value as shown at an instant $T_A$ in FIG. 3. When the dispersion is allowed to naturally stand, the evaporation of the water proceeds and a critical condition (B) as shown in FIG. 2 develops.

In this critical condition (B), solid fine particles 30 contact each other due to evaporation of water. Under the critical condition, the density of the fine solid particles 30 is at its highest, and the intensity of the scattered light is at a minimum. This critical condition is indicated at an instant $T_B$ in FIG. 3.

Figure 2:
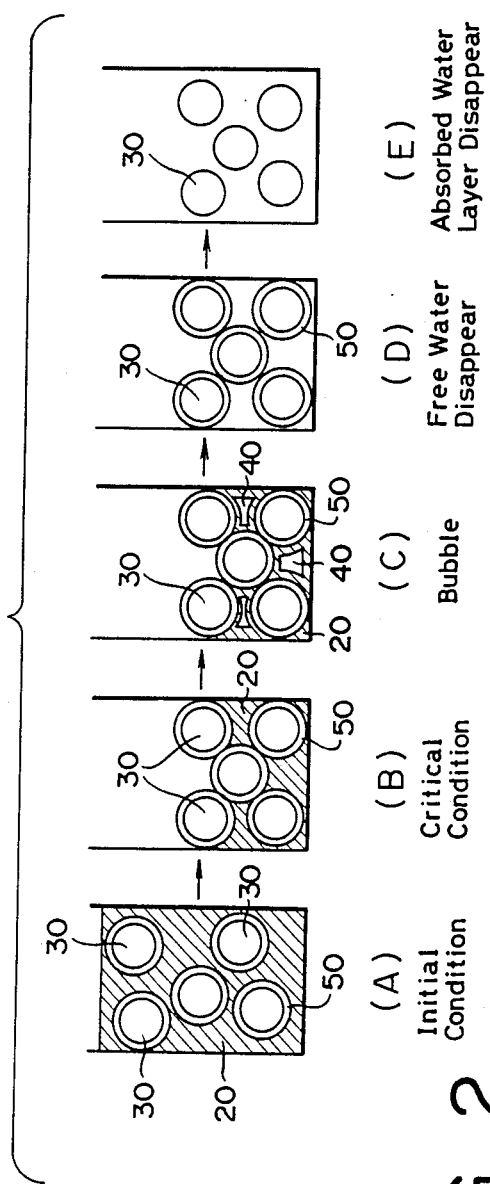
FIGS. 2A-2E are explanatory diagrams illustrating microscopically the principle of what change of a dispersion medium gives rise to a change in the intensity of a scattered light coming from a dispersion subjected to a method of the present invention.
Figure 3:
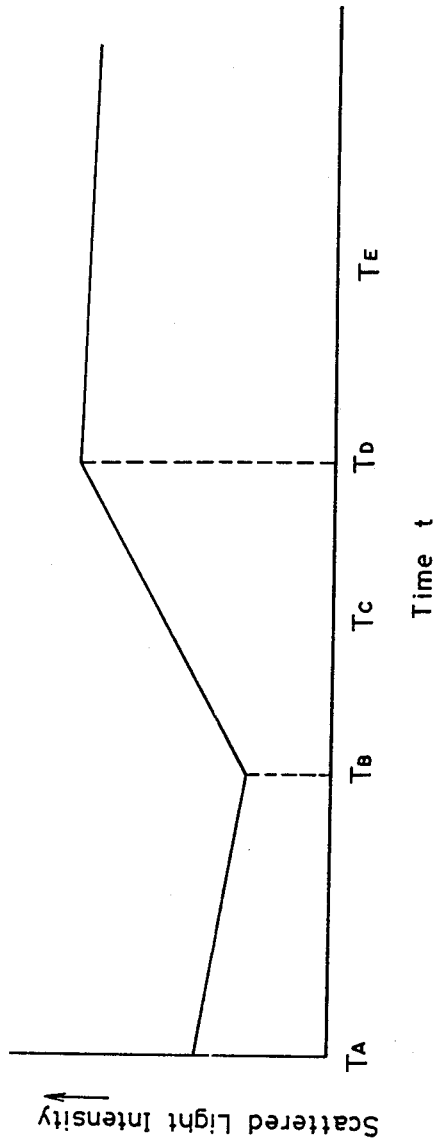
FIG. 3 is a characteristic curve illustrating a change in the intensity of a scattered light with time corresponding to the stages as shown in FIG. 2.

In the subsequent condition (C) as shown in FIG. 2, the evaporation of the water proceeds further and bubbles 40 are formed among the solid fine particles 30, and then in the next condition (D) as shown in FIG. 2, the free water 20 disappears. In a condition (E), absorbed water layers 50 formed around the solid fine particles 30 disappear. FIG. 3 shows their respectively corresponding instants $T_C$, $T_D$ and $T_E$.

The intensity of the scattered light gradually increases during the period ranging from $T_B$ to $T_D$, since the bubbles 40 are formed among the fine particles 30.

The intensity of the scattered light changes in the above-mentioned manner in the course of the dispersion phases as the dispersion medium is solidified with the disappearance of the water. Observation of the changes in the intensity of the scattered light, particularly the detection of a time period from the instant $T_A$ to the instant $T_B$, allows the water retentivity of the specimen or water absorbency of the water-absorbent material to be judged.

Figure 4:
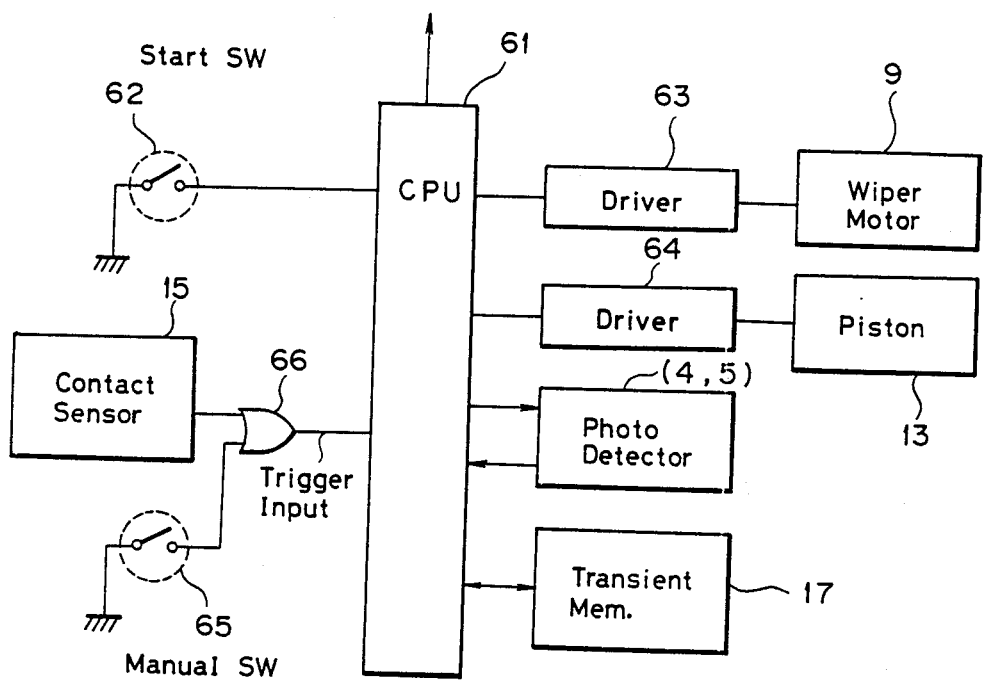
FIG. 4 is a block diagram showing an embodiment of an arrangement of a control circuit of an apparatus according to the present invention.

An embodiment of a control system for controlling an operating mechanism in a measurement apparatus according to the present invention will now be described with reference to FIG. 4. Reference numeral 61 denotes a central processing unit (CPU). Actuation of a start switch 62 makes the central processing unit 61 sequentially actuate the following members to carry out sequence control. A drive 63 drives the motor 9 for the wiper, and a driver 64 drives the piston 13. A manual switch 65 is for manual triggering. An output from the contact sensor 15 or the switch 65 is obtained as a trigger input from an OR gate 66, and supplied to the CPU 61, so that the transient memory 17 is triggered.

Figure 5:
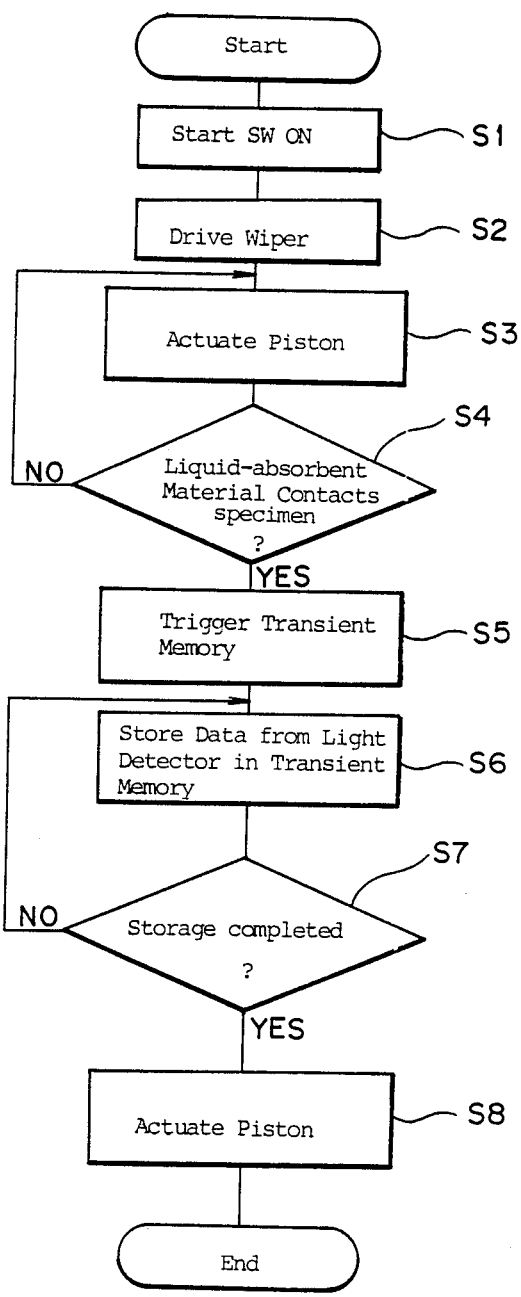
FIG. 5 is a flow chart showing an example of a control procedure of operations for measurement according to the present invention.

FIG. 5 shows an example of a measurement control procedure performed according to the present invention. When the start switch 62 is actuated at step S1, the wiper 6 is driven by the motor 9 at step S2. The wiper 6 sweeps a liquid overflowing the specimen chamber 3, and then is moved to a shunting position. Subsequently, at step S3, the piston 13 having the liquid-absorbent material 23 is actuated to descend.

The descending action is continued until the liquid-absorbent material 23 contacts the specimen 12 in the specimen chamber 3. Whether or not such contact occurs is judged at step S4. Upon such contact, the procedure proceeds to step S5, so that the transient memory 17 is triggered. At step S6, data of an intensity of the scattered light detected by the light receiving element 5 of the light detector are stored in the transient memory 17. The stored data are read out from the memory 17 and then applied via the CPU 61 to a display means (not shown), for example, a recorder, so that the data are recorded.

At step S7, whether or not the data for the predetermined period of time are stored is judged. After the completion of the storage, the procedure proceeds to step S8, at which the piston 13 having the liquid-absorbent material 23 is actuated to pull the liquid-absorbent material 23 upward. Then, the measurement is completed.

In the above-mentioned procedure, a duration of triggering the transient memory 17 is several tens of msec. around the instant of contact of the liquid-absorbent material 23 with the specimen 12. Thus, it is sufficient that the intensity of the scattered light is measured only during that duration.

The inventors of the present invention have confirmed through experiments that a degree of water absorption can be judged by the measurement within such an extremely short period of time.

Figure 6:
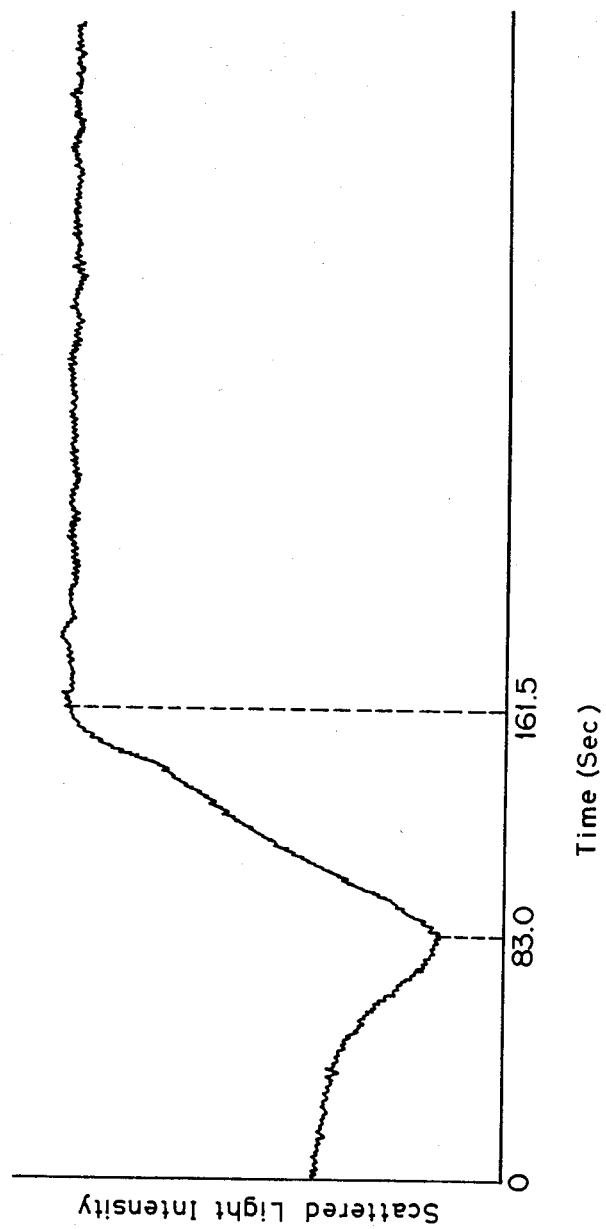
FIG. 6 is a characteristic curve illustrating a change in the intensity of a scattered light coming from a specimen, which change is measured by the apparatus according to the present invention when the specimen is allowed to naturally stand without contact thereof with any liquid-absorbent material.
Figure 7:
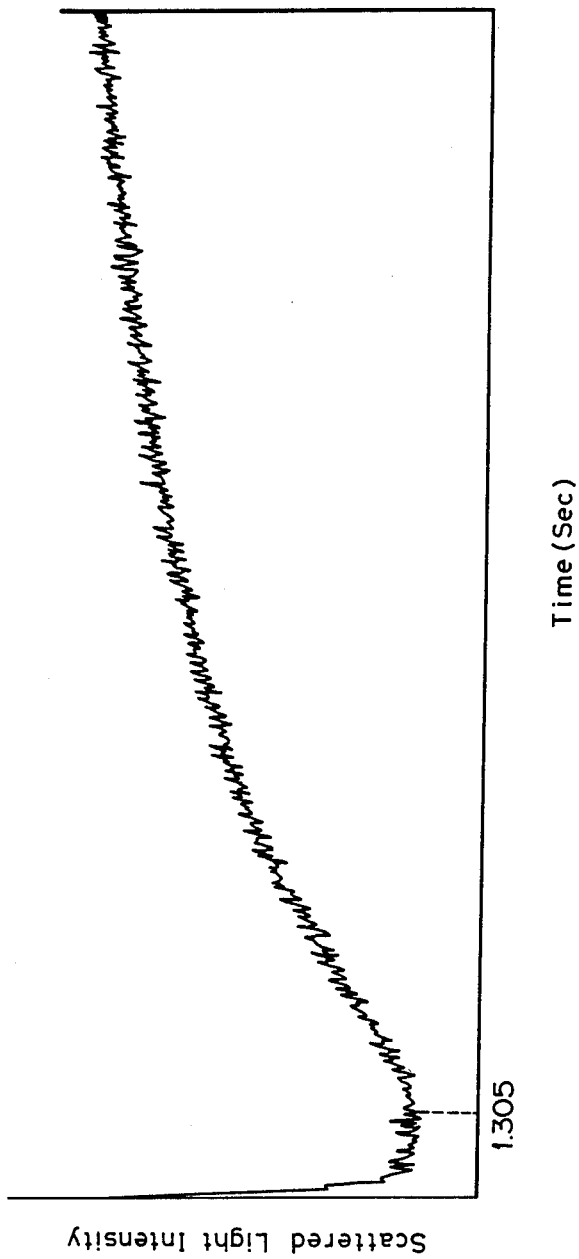
FIG. 7 is a characteristic curve illustrating a change in the intensity of a scattered light coming from a specimen which change is measured by the apparatus according to the present invention when a liquid-absorbent material is pressed to contact the specimen.

FIGS. 6 and 7 show data obtained by a comparative experiment. In this experiment, the specimen 12 was a suspension of a mixture of 61.85 g of clay, 0.15 g of sodium polyacrylate (thickener), and 38 g of water. The depth of the specimen chamber 3 was 50 $\mu$m. The water-absorbent material 23 was a commercially available noncoated paper (thickness: about 100 $\mu$m).

FIG. 6 shows results of a scattered light intensity measured in a spontaneously dried state of the specimen 12 without contact thereof with the water-absorbent material 23. In this case, the measurement was started just after making the surface of the specimen 12 flat with the wiper 6. The intensity of the scattered light was minimized after 83.0 sec. The subsequent measurement showed increasing intensities of the scattered light until 161.5 sec., at which the intensity was substantially stabilized, as shown in FIG. 6.

FIG. 7 illustrates a result when measurement was performed upon contact of the specimen 12 having a surface made flat in the same manner as described above with the descending liquid-absorbent material 23. The intensity of the scattered light was abruptly decreased and minimized after about 1.3 sec., followed by a gradual increase, as shown in FIG. 7.

As is apparent from these experimental results, the critical condition of the specimen can be grasped in an extremely short time by the method using the apparatus therefor according to the present invention. Additionally stated, the relationship between an absolute value of a speed of liquid movement and an intensity of the scattered light cannot be uniformly established, since it involves the relativity of the specimen and the water-absorbent material concerned. However, the liquid movement characteristics can be judged by comparison of values involved therein with measured data obtained using various specimens.

Specimens to which the method of the present invention is applicable include liquids, suspensions, solutions, and mixtures thereof, which at least partially comprises a liquid. For example, there can be mentioned a dispersion such as a slurry. As examples of solid fine particles constituting the dispersion phases of such a dispersion, there can be mentioned cement, clay, a wheat powder, and a polymer latex. As examples of the dispersion medium, there can be mentioned aqueous solutions of a hydrophilic polymer, such as solutions of casein, polyvinyl alcohol, starch, or polyacrylic acid. Specific practical examples of preferred specimens include a pigment dispersion for paper coating. Besides liquids including dispersion, pure water may be used as the specimen. Besides suspensions, solutions containing some matter dissolved therein as well as solutions including dispersions can be used.

Although the foregoing description is concerned with examination of separability of a dispersion medium in one of various dispersion specimens, or, in other words, liquid retentivity of a dispersion specimen, the applicability of the present invention is not limited to it. For example, the present invention can be effectively applied to examination of water absorbing capacities of various water-absorbent materials for a given specimen. In a field of, for example, the paper manufacturing industry, the apparatus of the present invention may be used not only as an apparatus for measuring the liquid retentivity of a coating but also as an apparatus for measuring the water absorbency of a base paper.

While the wiper 6 is automatically operated after placing the dispersion specimen in the specimen chamber 3 in the foregoing embodiment, a wiper blade may, of course, be manually operated instead of the automatic operation to wipe the specimen 12 filled in the specimen chamber 3 to provide a state wherein the specimen 12 is filled just up to the top of the opening of the specimen chamber 3.

As described above, according to the present invention, characteristics of mobility of liquid as the dispersion medium of a dispersion specimen is judged by the steps of filling the specimen in a specimen chamber formed in a specimen bed made of a transparent material just up to the level of the upper surface of the specimen bed, of pressing a liquid-absorbent material keeper for keeping a liquid-absorbent material horizontally to make the liquid-absorbent material contact with the specimen bed from the upper side of the specimen chamber, and of continuously detecting an intensity of a scattered light coming from the specimen in the specimen chamber with an optical detection means consisting of a light emitting source and a light receiver and being disposed on the side of the lower surface of the spe imen bed while the liquid-absorbent material is forced to contact the specimen bed. Thus, the characteristics of liquid mobility can be grapsed in a period of time extremely shorter than those obtained by a conventional method. Particularly, when an apparatus of the present invention is employed in connection with a coating technique in a paper manufacturing industry, observation can be made under a condition that the water-absorbent material is pressed, i.e., a condition which is similar to an environment involved in the coating step of paper manufacturing process, the present invention is suitable for measuring not only water retentivity of a coating but also water absorbency of a base paper.

What is claimed is:

1. A method of measuring a liquid mobility comprising the steps of:
   disposing a specimen at least partially containing liquid in a specimen chamber having a recessed form and made at least partially of a transparent material;
   pressing a liquid-absorbent material capable of absorbing said liquid against an opening of said specimen chamber to absorb said liquid;
   projecting a light onto one surface of said specimen in said chamber from a light source so that the projected light is scattered from said specimen;
   detecting an intensity of said scattered light coming from at least said one surface of said specimen; and
   measuring mobility characteristics of said liquid in accordance with a change in the intensity of said scattered light thus detected.

2. A method of measuring a liquid mobility as claimed in claim 1, wherein said specimen is a member selected from the group consisting of liquid, suspension, solution, and mixture thereof.

3. A method of measuring a liquid mobility as claimed in claim 1, wherein said light-absorbent material is a member selected from the group consisting of paper, pulp fiber, non-woven fabric, woven fabric, and foam, and further comprising the step of covering at least said opening of said specimen chamber.

4. A method of measuring a liquid mobility as claimed in claim 1, wherein said optical detection means comprises a light source and a photo detecting device, and further comprising the steps of:
directing said light from said light source at an angle not exceeding a critical angle over which total deflection occurs; and
receiving said scattered light when a light is projected from said light source to obtain an electrical signal corresponding to said scattered light.

5. A method of measuring a liquid mobility as claimed in claim 1, wherein said specimen is a member selected from the group consisting of liquid, suspension, solution, and mixture thereof, and wherein said liquid-absorbent material is a member selected from the group consisting of paper, pulp fiber, non-woven fabric, woven fabric, and foam, said method further comprising the step of covering at least said opening of said specimen chamber.

6. A method of measuring liquid mobility as claimed in claim 5, wherein said optical detection means comprises a light source and a photo detecting device, and further comprising the steps of:
directing said light at an angle not exceeding a critical angle over which total reflection occurs; and
receiving said scattered light when a light is projected from said light source to obtain an electrical signal corresponding to said scattered light.

7. A method of measuring a liquid mobility as claimed in claim 1, wherein said liquid-absorbent material is a member selected from the group consisting of paper, pulp fiber, non-woven fabric, woven fabric, and foam, and can cover at least said opening of specimen chamber, and said optical detection means comprises a light source and a photo detecting device, said method further comprising the steps of:
covering at least said opening of said specimen chamber with said liquid-absorbent material;
directing said light at an angle not exceeding a critical angle over which total reflection occurs; and
receiving said scattered light when a light is projected from said light source to obtain an electrical signal corresponding to said scattered light.

8. A method of measuring a liquid mobility as claimed in claim 1, wherein said light from said light source is incident to said specimen at an angle not exceeding a critical angle of total reflection.

9. An apparatus for measuring a liquid mobility comprising:
a specimen chamber having an opening in one surface thereof for inserting a specimen at least partially containing a liquid, said specimen chamber being made at least partially of a transparent material;
means for retaining a liquid-absorbent material capable of absorbing liquid contained in said specimen and for pressing said liquid-absorbent material against said opening of said specimen chamber;
an optical detection means arranged on the opposite side of said specimen chamber from said one surface, said detection means including a light source for projecting a light onto said specimen and a detector for detecting an intensity of a scattered light coming from said specimen;
a trigger means for detecting when said liquid-absorbent material contacts said specimen chamber to produce a trigger signal for triggering said optical detection means; and
means for storing data indicative of the intensity of said scattered light detected by said optical detection means in response to said trigger signal.

10. An apparatus for measuring a liquid mobility as claimed in claim 9, wherein said specimen is a member selected from the group consisting of liquid, suspension, solution, and mixture thereof.

11. An apparatus for measuring a liquid mobility as claimed in claim 9, wherein said liquid-absorbent material capable of absorbing said liquid is a member selected from the group consisting of paper, pulp fiber, non-woven fabric, woven fabric, and foam, and can cover at least said opening of said specimen chamber.

12. An apparatus for measuring a liquid mobility as claimed in claim 9, wherein said optical detection means comprises a light source directing said light at an angle not exceeding a critical angle over which total reflection occurs and a photo detecting device receiving said scattered light when a light is projected from said light source to obtain an electrical signal corresponding to said scattered light.

13. An apparatus for measuring a liquid mobility as claimed in claim 9, wherein said optical detection means comprises a light source directing said light at an angle not exceeding a critical angle over which total reflection occurs and a photo detecting device receiving said scattered light when a light is projected from said light source to obtain an electrical signal corresponding to said scattered light and wherein said specimen chamber is a flat recess which has a diameter of 1 to 2 cm and a depth of 1 mm or less and is formed in a transparent specimen bed having a smooth surface and a thickness of 1 to 30 mm and made of glass, silica, transparent resin, or the like.

14. An apparatus for measuring a liquid mobility as claimed in claim 13, wherein said specimen is a member selected from the group consisting of liquid, suspension, solution, and mixture thereof.

15. An apparatus for measuring a liquid mobility as claimed in claim 13, wherein said liquid-absorbent material capable of absorbing said liquid is a member selected from the group consisting of paper, pulp fiber, non-woven fabric, woven fabric, and foam, and can cover at least said opening of said specimen chamber.

16. An apparatus for measuring a liquid mobility as claimed in claim 9, wherein said light from said light source is incident to said specimen at an angle not exceeding a critical angle of total reflection.

17. An apparatus for measuring a liquid mobility as claimed in claim 9, wherein said specimen chamber is a flat recess which has a diameter of 1 to 2 cm and a depth of 1 mm or less and is formed in a transparent specimen bed having a smooth surface and a thickness of 1 to 30 mm and made of glass, silica, transparent resin, or the like.

* * * * *